United States Patent [19]
Cobb

[11] 3,987,056
[45] Oct. 19, 1976

[54] DISPROPORTIONATION OF N-ARYL-1,2,3,6-TETRAHYDROPHTHALIMIDES

[75] Inventor: Raymond L. Cobb, Bartlesville, Okla.

[73] Assignee: Phillips Petroleum Company, Bartlesville, Okla.

[22] Filed: May 7, 1973

[21] Appl. No.: 357,643

[52] U.S. Cl. .................. 260/326 R; 260/326 HL; 260/326 A
[51] Int. Cl.$^2$ ...................................... C07D 209/48
[58] Field of Search ...... 260/326 R, 326 A, 326 HL

[56] References Cited
UNITED STATES PATENTS

| | | | |
|---|---|---|---|
| 2,900,243 | 8/1959 | Lowis | 260/326 |
| 3,287,427 | 11/1966 | Karol | 260/666 A |
| 3,557,132 | 1/1971 | Herman et al. | 260/302 |
| 3,745,170 | 7/1973 | Fujinami | 260/326.5 S |

FOREIGN PATENTS OR APPLICATIONS

| | | |
|---|---|---|
| 1,425,589 | 12/1965 | France |
| 51,866 | 9/1969 | Romania |

OTHER PUBLICATIONS

S. Carru et al., Tet. Letters, 1967, 1079–1082.
E. O. Turgel et al. Chem. Abs. 66, 66937e (1967).
M. S. Nemtsov et al. Chem. Abs. 65, 13948H (1966).
M. S. Nemtsov et al. Chem. Abs. 56, 572 (1961).
Schukerman, Chem. Abs. 53, 6163g (1956).

*Primary Examiner*—Alton D. Rollins
*Assistant Examiner*—Mark L. Berch

[57] ABSTRACT

N-Aryl-1,2,3,6-tetrahydrophthalimides are disproportionated to N-arylphthalimides and N-arylhexahydrophthalimides employing a catalyst of palladium, platinum, or ruthenium, on carbon.

11 Claims, No Drawings

DISPROPORTIONATION OF N-ARYL-1,2,3,6-TETRAHYDROPHTHALIMIDES

FIELD OF THE INVENTION

The invention relates to the disproportionation of N-aryl-1,2,3,6-tetrahydrophthalimides.

BACKGROUND OF THE INVENTION 1,2,3,6-Tetrahydrophthalic anhydride undergoes double bond isomerization to 3,4,5,6-tetrahydrophthalic anhydride at moderate temperatures. At higher temperatures, this anhydride disproportionates to produce cyclohexane dicarboxylic anhydride and phthalic anhydride. However, disproportionation of N-aryl-1,2,3,6-tetrahydrophthalimides has not heretofore been feasible, even though such disproportionation potentially is valuable for preparing a variety of herbicidal chemicals as well as for end products useful in other applications.

BRIEF SUMMARY OF THE INVENTION

I have discovered, unexpectedly, that N-aryl-1,2,3,6-tetrahydrophthalimide can be disproportionated over a palladium, platinum, or ruthenium catalyst on carbon at very moderate temperatures, without double bond isomerization, to produce a mixture of N-arylhexahydrophthalimide and N-arylphthalimide. The moderate temperature reaction avoids decomposition reactions of the reactants and/or end products. The process takes place without the formation of any detectable amounts of double bond isomer.

DETAILED DESCRIPTION OF THE INVENTION

In accordance with my invention, N-aryl-1,2,3,6-tetrahydrophthalimides are disproportionated over a palladium, platinum, or ruthenium, or combinations thereof on carbon catalyst at contacting temperature of up to about 200° C., preferably for ease of handling about 150° C. to 200° C., more preferably for smoothness of reaction and avoidance of side reactions about 165° to 185° C.

The general reaction involved in the present process can be represented as follows:

In the above equations, each R can be individually selected from hydrogen, or alkyl, cycloalkyl, aryl, alkoxy, halogen, or combination of such groups, and halogen may include fluorine, chlorine, bromine, or iodine, with the proviso that not more than two R groups can be other than hydrogen, and when two R groups other than hydrogen are present in (V), not more than one of these can be in the 2 or 6 positions. The total number of carbon atoms in the aromatic amine reactant (V) can be as desired or convenient for handling purposes, preferably in the range of about 6 to 16. Suitable aromatic amine reactants (V) include aniline, p-toluidine, p-chloroaniline, p-cyclohexylaniline, o-anisidine, p-bromoaniline, p-(1-naphthyl)aniline, 4-aminobiphenyl, p-fluoroaniline, m-isobutylaniline, 2,4-dimethylaniline, 3,4-dichloroaniline, 2,5-diethoxyaniline, p-iodoaniline, 4-amino-4'-isobutylbiphenyl, and the like.

The catalysts I employ in the process of my invention comprise palladium, platinum, or ruthenium, or combination on carbon or carbon-containing substrate, presently preferred being charcoal. These catalysts are readily prepared by means known to the catalyst arts, such as by reduction of a palladium, platinum, or ruthenium metal compound such as the metal halide on carbon. For example, palladium chloride on charcoal can be readily hydrogenated to give palladium on charcoal.

The catalysts I employ can vary widely in composition, though preferably containing about 0.5 to 20 weight percent of palladium, platinum, or ruthenium, or combination based on the carbon or charcoal substrate, more preferably about 5 to 15 weight percent, and particularly presently I prefer about 10 weight percent.

In the process of my invention, I presently prefer a weight ratio of palladium, platinum, or ruthenium, or combination to starting compound (I) of about 0.01 to 2 per 100, preferably 0.03 to 0.3 part of metal per 100 parts of starting compound.

For convenience, temperatures employed in my reaction preferably are above the melting point of the starting materials when working in the absence of diluent. However, where desired, suitable diluent may be employed, and exemplary of these are biphenyl, naphthalene, diphenyl ether, mixtures thereof, similar high boiling homologues, and the like.

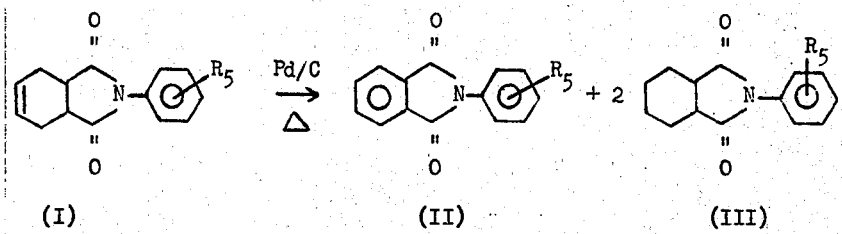 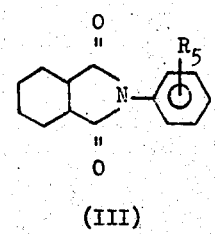

(I)　　　　　(II)　　　　　(III)

Suitable starting materials for the invention may be readily prepared by methods known to the art, such as by the general reaction illustrated below:

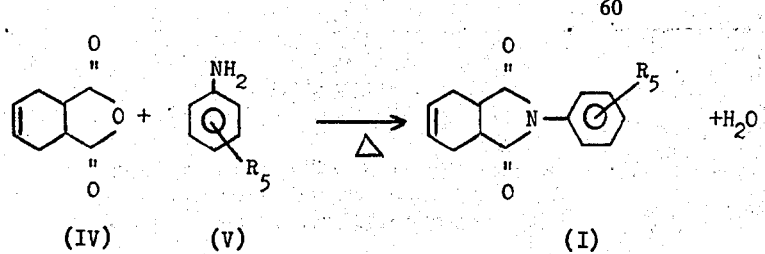 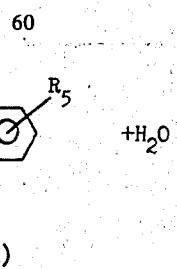

(IV)　　(V)　　　　　(I)

The starting material (I) is contacted with the catalyst preferably at a temperature sufficiently above the melting point of the starting material so as to maintain liquid phase, or otherwise at convenient temperatures where diluent is used, presently preferring contacting temperatures of less than about 200° C., more preferably of about 150° to 200° C., more preferably about 165° to 185° C.

Operating pressures preferably should be on the order of about 1 atmosphere, though higher or lower pressures can be used if desired, depending on the starting materials, whether diluent is employed, and the like, and operating temperatures. Operation at elevated temperatures above about 200° C. may result in excessive decomposition or change the course of reaction, while operating at temperatures below the suggested range may make it difficult to maintain suitable liquid phase conditions. The contacting process preferably is conducted under an inert atmosphere, such as nitrogen or inert rare gas, to avoid formation of oxidative type by-products.

Contacting times for my reaction can vary over a wide range though presently suggested are times in the range of up to about 24 hours, such as about 2 to 24 hours, presently preferred about 5 to 10 hours. Unconverted materials can be separated and recycled to the reactor if desired.

EXAMPLE

Particular materials employed, particular species, ratios employed should be considered illustrative, and not limitative, of the reasonable scope of my invention as described in the specification and claims.

Example I

N-Phenyl-1,2,3,6-tetrahydrophthalimide was prepared by condensation of aniline and 4-cyclohexene-1,2-dicarboxylic anhydride in xylene solvent, according to known methods such as cited in 54 *Chem. Abstr.* 9886 (1960).

150 Grams of the N-phenyl-1,2,3,6-tetrahydrophthalimide was treated with 2 grams of 10 weight percent palladium-on-carbon catalyst in a stirred reactor equipped with nitrogen atmosphere and condenser. The reaction mixture was heated with stirring under nitrogen for between 6 and 7 hours at a temperature of about 175° C. Hot benzene/tetrahydrofuran admixture then was added to the reaction mixture to facilitate separation of catalyst upon filtration, and the resulting admixture filtered to remove catalyst residues.

On cooling to room temperature, the filtrate gave 23 grams of a crystalline solid which exhibited a melting point of 206°-207° C. The melting point for pure N-phenylphthalimide is recorded as 208°-210° C. according to *Lange's Handbook of Chemistry*, 6th Edition (1946).

Removal of the solvent from the filtrate remaining after removal of the N-phenylphthalimide gave a residue which, after recrystallization from toluene, gave 93 grams of an off-white solid melting at about 125° C. A further crystal product weighing 15 grams with a melting point of about 121°-123° C. was isolated from the mother liquor remaining from the toluene recrystallization. Recrystallization of the first 93 grams of solid from the toluene recrystallization gave 85 grams of cream-colored crystals melting at 125°-127° C. This material by nuclear magnetic resonance and mass spectral analyses was shown to be a mixture of 80 weight percent N-phenylhexahydrophthalimide and 20 weight percent N-phenylphthalimide.

This example illustrates the unexpected nature of my invention, namely the disproportionation of N-aryl-1,2,3,6-tetrahydrophthalimide over the defined catalysts at quite moderate temperatures. None of the double bond isomer N-phenyl-3,4,5,6-tetrahydrophthalimide was detectable in the product mixture.

As exemplary of the desirability of the end products, using N-4-chlorophenyl-1,2,3,6-tetrahydrophthalimide as exemplary starting material in my disproportionation process, I can prepare the known herbicide N-4-chlorophenylhexahydrophthalimide effectively and efficiently. End products from related starting materials have similar applications. Other end products are useful as antiknock compounds, and the like.

Certainly, reasonable variations and modifications of my invention are possible yet still within the scope of my disclosure and without departing from the intended scope and spirit thereof.

I claim:

1. The liquid phase process for preparing (II) N-phenylphthalimides or N-substituted phenylphthalimides and (III) N-phenylhexahydrophthalimides or N-substituted phenylhexahydrophthalimides represented by formulas (II) and (III)

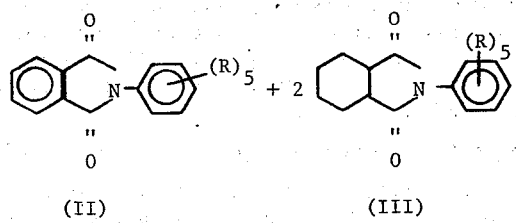

which process comprises contacting (I) N-phenyl-1,2,3,6-tetrahydrophthalimides or N-substituted phenyl-1,2,3,6-tetrahydrophthalimides represented by (I):

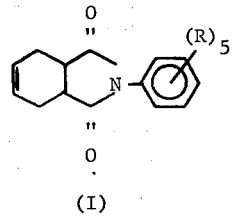

wherein each R is independently hydrogen, or an alkyl, cycloalkyl, aryl, alkoxy, halogen, such that at least three R groups are hydrogen, and when two R groups other than hydrogen are present in (I), not more than one of these can be in the 2 or 6 positions, and wherein the total number of carbon atoms in said (I) is in the range of 14 to 24, with a palladium, platinum, ruthenium, or combination thereof -on-carbon catalyst at a contacting temperature of less than about 200° C effective for the conversion of said (I) tetrahydrophthalimide to said (II) phthalimide and (III) hexahydrophthalimide.

2. The process according to claim 1 wherein said contacting temperature is between about 150° and 200° C., and wherein said process employs a palladium or platinum or ruthenium:starting compound (I) weight ratio of approximately 0.01–2 parts metal to 100 parts starting compound.

3. The process according to claim 2 wherein said catalyst represents about 0.5 to 20 weight percent palladium, platinum, or ruthenium relative to carbon.

4. The process according to claim 3 wherein said contacting temperature is about 165° to 185° C. and said metal to starting compound ratio is about 0.03 to 0.3 part of metal per 100 parts of starting compound.

5. The process according to claim 4 wherein said catalyst comprises palladium on charcoal.

6. The process according to claim 5 wherein in said (I) each R is hydrogen such that said (I) is N-phenyl-1,2,3,6-tetrahydrophthalimide, and the products are (II) N-phenylphthalimide and (III) N-phenylhexahydrophthalimide.

7. The process according to claim 4 wherein said catalyst comprises platinum on carbon.

8. The process according to claim 4 wherein said catalyst comprises ruthenium on carbon.

9. The process according to claim 2 further employing a diluent which is biphenyl, naphthalene, diphenyl ether, or mixtures thereof.

10. The liquid phase conversion of a tetrahydrophthalimide represented by (I)

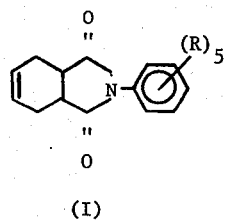

(I)

wherein R is hydrogen, or alkyl, cycloalkyl, aryl, alkoxy, or halogen radical, such that at least three R groups are hydrogen and when two R groups other than hydrogen are present in (I), not more than one of these can be in the 2 or 6 positions, to (II) phthalimides and (III) hexahydrophthalimides represented by

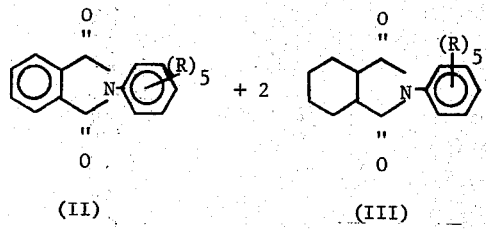

(II)            (III)

wherein said conversion is effectuated by contacting said (I) at a temperature of about 150° to 200° C. with an effective amount of a catalyst consisting essentially of ruthenium-on-carbon, wherein said effective amount of said catalyst is approximately 0.01–2 parts ruthenium per 100 parts starting (I) phthalimide.

11. The liquid phase process for preparing (II) N-4-chlorophenylphthalimide and (III) N-4-chlorophenylhexahydrophthalimide which process comprises contacting (I) N-4-chlorophenyl-1,2,3,6-tetrahydrophthalimide with a palladium-on-charcoal catalyst at a contacting temperature in the range of about 165°–185° C. effective for the conversion of said (I) tetrahydrophthalimide to said (II) phthalimide and (III) hexahydrophthalimide, wherein said process employs a palladium: starting compound (I) weight ratio of approximately 0.03 to 0.3 parts metal to 100 parts starting compound by weight.

* * * * *